(12) United States Patent
Haase et al.

(10) Patent No.: US 11,875,429 B2
(45) Date of Patent: Jan. 16, 2024

(54) TOMOGRAPHIC X-RAY IMAGE RECONSTRUCTION

(71) Applicant: KONINKLIJKE PHILIPS N.V., Eindhoven (NL)

(72) Inventors: Christian Haase, Hamburg (DE); Michael Grass, Buchholz In der Nordheide (DE); Dirk Schaefer, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 716 days.

(21) Appl. No.: 17/040,744

(22) PCT Filed: Mar. 18, 2019

(86) PCT No.: PCT/EP2019/056644
§ 371 (c)(1),
(2) Date: Sep. 23, 2020

(87) PCT Pub. No.: WO2019/185380
PCT Pub. Date: Oct. 3, 2019

(65) Prior Publication Data
US 2021/0012545 A1 Jan. 14, 2021

(30) Foreign Application Priority Data
Mar. 28, 2018 (EP) .................................. 18164466

(51) Int. Cl.
| | | |
|---|---|---|
| *G06T 11/00* | (2006.01) | |
| *A61B 6/03* | (2006.01) | |
| *A61B 6/00* | (2006.01) | |
| *G06T 7/00* | (2017.01) | |
| *G06F 18/22* | (2023.01) | |

(52) U.S. Cl.
CPC ............ *G06T 11/005* (2013.01); *A61B 6/032* (2013.01); *A61B 6/4028* (2013.01); *A61B 6/463* (2013.01);
(Continued)

(58) Field of Classification Search
CPC .......................... G06F 18/22; G06T 2211/412
See application file for complete search history.

(56) References Cited

U.S. PATENT DOCUMENTS 5,802,220 A * 9/1998 Black ...................... G06T 7/215
382/293
9,782,141 B2 * 10/2017 Yu .......................... A61B 5/702
(Continued)

OTHER PUBLICATIONS

Berger, M., et al. "Marker-free Motion Correction in Weight-bearing Cone-beam CT of the Knee Joint." Medical Physics, vol. 43, No. 3, Mar. 2016, pp. 1235-1248. DOI.org (Crossref), https://doi.org/10.1118/1.4941012. (Year: 2016).*
(Continued)

*Primary Examiner* — Matthew C Bella
*Assistant Examiner* — Johnny B Duong (57) ABSTRACT

An apparatus for image reconstruction that includes input circuitry configured to acquire, from an image sequence, first and second 2D projection data of a region of interest of an object at respective acquisition times; and provide first 3D object data of a first object in a region of interest and second 3D object data of a second object in a region of interest. The apparatus also includes a processor configured to generate a first registration of the first and/or second 3D object data to the first 2D projection data and a second registration of the first and/or second 3D object data to the second 2D projection data; provide a vector field defining motion of the second object relative to the first object between the acquisition times based on the registrations; generate corrected projection data using the vector field; and generate a motion-compensated image sequence based on the corrected projection data.

14 Claims, 6 Drawing Sheets

(52) U.S. Cl.
CPC .......... *A61B 6/501* (2013.01); *A61B 6/5264* (2013.01); *A61B 6/54* (2013.01); *G06F 18/22* (2023.01); *G06T 7/0012* (2013.01); *G06T 11/008* (2013.01); *G06T 2207/10081* (2013.01); *G06T 2207/30008* (2013.01)

(56) References Cited

U.S. PATENT DOCUMENTS

| | | |
|---|---|---|
| 2016/0128624 A1 | 5/2016 | Matt |
| 2016/0262711 A1 | 9/2016 | Nyholm et al. |
| 2017/0000430 A1 | 1/2017 | Lu et al. |

OTHER PUBLICATIONS

Müller, Kerstin, et al. "Evaluation of Interpolation Methods for Surface-Based Motion Compensated Tomographic Reconstruction for Cardiac Angiographic C-Arm Data . . . " Medical Physics, vol. 40, No. 3, Feb. 2013, p. 031107. DOI.org (Crossref), https://doi.org/10.1118/1.4789593. (Year: 2013).*

Xu, Di, et al. "2D/3D Registration for X-Ray Guided Bronchoscopy Using Distance Map Classification." 2010 Annual International Conference of the IEEE Engineering in Medicine and Biology, 2010, pp. 3715-3718. IEEE Xplore, https://doi.org/10.1109/IEMBS.2010.5627657. (Year: 2010).*

Hill, Derek L. G., et al. "Medical Image Registration." Physics in Medicine & Biology, vol. 46, No. 3, Mar. 2001, p. R1. Institute of Physics, https://doi.org/10.1088/0031-9155/46/3/201. (Year: 2001).*

PCT/EP2019/056644 ISR & WO, Apr. 17, 2019, 13 Page Document.

Grass et al.: "Motion Compensation for Non-Gated Helical Ct: Application To Lung Imaging"; Medical Imaging 2018, Physics of Medical Imaging, Proc. of Spie vol. 10573, p. 105733H-1-105733H-6.

Ouadah et al.: "Correction of Patient Motion in Cone-Beam Ct Using 3D-2D Registration": Phys Med. Biol., 62, 2017, pp. 8813-8831.

* cited by examiner

TOMOGRAPHIC X-RAY IMAGE RECONSTRUCTION

CROSS-REFERENCE TO PRIOR APPLICATIONS

This application is the U.S. National Phase application under 35 U.S.C. § 371 of International Application No. PCT/EP2019/056644, filed on Mar. 18, 2019, which claims the benefit of European Patent Application No. 18164466.7, filed on Mar. 28, 2018. These applications are hereby incorporated by reference herein.

FIELD OF THE INVENTION

This invention relates generally to an apparatus for tomographic X-Ray image reconstruction, a method for tomographic image reconstruction, a C-arm X-Ray imaging system, a computer program element, and a computer readable medium.

BACKGROUND OF THE INVENTION

A rotational C-arm system for tomographic X-Ray image acquisition comprises an X-Ray source and an X-Ray detector arranged to face each other, typically separated by a C-arm gantry. A region of interest of a patient may be positioned in-between the X-Ray source and X-Ray detector. A two-dimensional X-Ray detector enables a "cone-beam" tomographic acquisition to be made.

In a cone-beam tomographic acquisition, the C-arm is rotated around an imaging plane of a patient in the region of interest. At a plurality of increments of the C-arm's rotation, the X-Ray source and X-Ray detector provide a two-dimensional projection view through the patient. An image reconstruction algorithm such as filtered back projection, or an iterative reconstruction algorithm, is applied to the sequence of two-dimensional projections. This enables a three-dimensional image of the patient in the region of interest to be provided from the sequence of two-dimensional projection views.

A C-arm acquisition protocol can typically take up to 30 seconds, and it cannot be excluded that the patient moves during this time. The result of patient motion during the C-arm acquisition protocol is a series of artefacts introduced at the 3D image reconstruction stage.

US 2017/0000430 A1 proposes an apparatus for imaging the head of a patient. The skull of a patient is fitted with head markers. At least one camera acquires a motion study of the patient's jaw. Control logic processor in communication with the apparatus reconstructs volume image content using a sequence of 2D radiographic projection images in combination with a signal from the camera in order to segment the jawbone structure from the skull bone structure. However, such systems can be further improved.

SUMMARY OF THE INVENTION

Accordingly, it would be advantageous to provide an improved technique for tomographic X-Ray imaging. Therefore, according to a first aspect, there is provided an apparatus for tomographic image reconstruction. The apparatus comprises:
  an input unit; and
  a processing unit.

The input unit is configured to acquire, from an input projection image sequence, first and second 2D X-Ray projection data of a region of interest of an object acquired, respectively at first and second acquisition times, and the input unit is configured to provide (i) first 3D rigid object data of, or approximating, a first rigid object in a region of interest of a patient, and (ii) second 3D rigid object data of, or approximating, a second rigid object in a region of interest of a patient.

The processing unit is configured to generate a first registration of the first and/or second 3D rigid object data to the first 2D X-Ray projection data, to generate a second registration of the first and/or second 3D rigid object data to the second 2D X-Ray projection data, to estimate the relative motion of the second rigid object relative to the first rigid object occurring between the first and second acquisition times, and providing a relative motion vector field defining the estimated motion of the second rigid object relative to the first rigid object based on the first and second registrations, to generate corrected 2D X-Ray projection data using the relative motion vector field to correct for the motion of the second rigid object relative to the first rigid object during acquisition of the input projection image sequence, and to generate motion-compensated 3D reconstruction data of the input projection image sequence based on the corrected 2D X-Ray projection data.

Accordingly, an initial reconstruction or a 3D model of a first 3D rigid object in the region of interest, in combination with an initial reconstruction of a 3D model of a second 3D rigid object, may be used to more accurately tomographically reconstruct a sequence of 2D projection images. Primarily, the movement of the first 3D rigid object relative to the second 3D rigid object during a long acquisition protocol may be corrected in a simplified way using the knowledge that voxel points associated with a first 3D rigid object move with respect to a first rigid frame of reference, and that voxel points associated with a second 3D rigid object move with respect to a second rigid frame of reference.

For example, a human skull may be regarded as comprising two rigid structures. The bones of the neurocranium and the vomer, nasal bones, maxilla, and lacrimal bones may be considered to form part of a first 3D rigid object. The mandible may be considered to form part of a second 3D rigid object. The mandible is joined to the neurocranium at the two opposite masseter sections forming the two mandibular notches hinged to the temporalis areas on either side of the neurocranium.

Accordingly, a tomographic X-Ray reconstruction algorithm according to the first aspect recognizes that two rigid objects with a predictable interconnection are present in the sequence of 2D projection images acquired by a C-arm imaging system, for example. According to the first aspect, patient motion during a C-arm imaging protocol may be more effectively compensated in the in the 2D projection image sequences, resulting in an improvement in the quality of the 3D reconstructed image, without requiring an external marker. A reduction in a search space during registration taking into account the relationship between two rigid objects infers a lower computational load, and thus a lower latency when reconstructing the image, and/or a lower processor speed specification, for example.

Optionally, the first and/or second 3D rigid object data is acquired by the input unit from (i) an initial 3D reconstruction of the input projection image sequence, or (ii) a prior 3D imaging scan of the region of interest of the patient.

Accordingly, a variety of sources may be used to provide the starting data of the reconstruction algorithm. Even in the case that an initial 3D image reconstructed using 2D projections from a moving patient could contain some artifacts, the first and second rigid objects can still be distinguished to an extent useful enough for an initial reconstruction. Of course, a prior 3D imaging scan could provide data from the same acquisition device, or another device, providing flexibility of input data sources.

Optionally, the first and/or second 3D rigid object data is acquired by the input unit from a database of anatomical models.

Accordingly, an initial estimate of the form of the first and second rigid objects can be simply provided without extensive signal processing. In the exemplary case of a skull, the neurocranium and the mandible have somewhat unique shape characteristics across many patients, and thus generic first and second rigid models, optionally parameterizable in size, having the shape of the target anatomy may be provided in a simpler way than performing signal processing. Such an approach could be beneficial if the reconstruction artifacts caused by patient motion during an acquisition of the input projection image sequence is such that it is not possible to initially extract first and second rigid object data from them.

Optionally the input unit is configured to provide a motion model prior of the first and/or second rigid object, wherein the motion model prior defines a subset of a total set of possible motion trajectories of the first and/or second rigid object; and the processing unit is further configured to estimate the relative motion of the second rigid object relative to the first rigid object using, at least in part, the motion model prior to restrict the possible number of motion trajectories of the second rigid object considered in the estimate.

Accordingly, prior anatomical knowledge of the motion trajectory relationship between first and second rigid objects imaged in the region of interest may be used to restrict a search space during the 2D to 3D registration, and thus enable quicker image reconstruction. Using the example of the human skull, the motion relationship between the neurocranium and a mandible is defined principally by the motion restriction caused by the hinged attachment of the mandible to the neurocranium. This restricts the relative motion of the mandible to a declination of roughly 50 degrees from the jaw being closed to open. A smaller effect is that the mandible may pivot laterally (yaw) with respect to the neurocranium around ten degrees to either side. These restrictions on the motion of the mandible may be used, a priori, to restrict the search space when considering possible patient jaw motion occurring within an input sequence acquisition. Of course, the mentioned angle restrictions are one example of a restriction of a motion model suitable for a jaw. The skilled person will appreciate that similar models may be provided in respect of hip movement, knee movement, and others.

Optionally, the processing unit is further configured to generate the first registration by providing forward projection data of the first 3D rigid object data, generating a similarity metric representing the similarity of the forward projection data to the first X-Ray projection data, and registering the first rigid object in the first 3D anatomical data to the first X-Ray projection data using the similarity metric.

Accordingly, a plurality of 2D projections of the 3D rigid object data from different angles may be generated and compared to a captured 2D projection in a single frame of the input image sequence. Each of the plurality of 2D projections will have a slightly different shape. The shape of the 2D projection matching the particular captured 2D projection in the input image sequence most closely matching may be identified (according, for example, to a shape comparison, an area comparison, or many others). The angle of the projection in the plurality of 2D projections that generates the best match to the captured 2D projection in the input image sequence reveals the orientation of the first 3D rigid object at the time instant of acquisition of the captured 2D projection. This process may also be applied to the second 3D rigid object data, or others.

Optionally, estimating the relative motion of the second rigid object relative to the first rigid object occurring between the first and second acquisition times further comprises identifying a first rigid motion curve of the second rigid object by comparing a subsequent position of the second rigid object in the second 2D X-Ray projection data to an initial position of the second rigid object in the first 2D X-Ray projection data.

Accordingly, the relationship between a starting position of a second rigid object and a finishing position can simplify the estimation of a motion trajectory between the first rigid object and the second rigid object.

Optionally, the processing unit is further configured to estimate the motion of the first rigid object relative to the second rigid object by defining a spatially intermediate portion of the first and/or second 2D X-Ray projection data in-between the first and second rigid objects, identifying a second rigid motion curve of the first rigid object in the spatially intermediate portion by comparing a subsequent position of the first rigid object in the second 2D X-Ray projection data as compared to an initial position of the first rigid object in the first 2D X-Ray projection data, and generating a rigid composite motion curve as a combination of the first and second rigid motion curves.

Consequently, in an intermediate region between two rigid objects, the motion curves of the first and second rigid objects may be calculated as a combination of the motion of the two rigid objects.

Optionally, the processing unit is further configured to correct 2D X-Ray projection data based upon the motion vector field of the second rigid data.

Accordingly, a simplifying assumption may be made that the first rigid object is substantially still, but that the second rigid object is in motion. Such an assumption may hold in the example of a neurocranium and mandible when, for example, a patient suffers from a severe tremor affecting the mandibular muscles.

Optionally, the processing unit is further configured to estimate the absolute motion of the first rigid object and the second rigid object relative to the imaging geometry, provide an absolute motion vector field defining the estimated motion of the first and second rigid objects relative to the imaging geometry, and generate the corrected 2D X-Ray projection data additionally using the absolute motion vector field combined with the relative motion vector field.

Accordingly, the motion of the first and second rigid objects relative to the same coordinate system of the imaging geometry may be calculated.

In other words, there are provided at least two corrected acquisition trajectories which are used for the reconstruction of two 3D volumes. One trajectory represents the first rigid object, and the second represents the second rigid object. A final 3D reconstruction is generated as a combination of the two 3D volumes, for example, by using an interpolation method for the spatially intermediate locations, or a third reconstruction using the interpolated intermediate trajectory.

The term "2D X-Ray projection data" may refer to 2D projection data with a corrected trajectory.

Optionally, the apparatus further comprises an output unit, wherein the output unit is further configured to display the motion-compensated 3D reconstruction data to a user.

Accordingly, a user of an imaging system can view the improved image reconstruction.

Optionally, the first rigid data comprises an initial 3D reconstruction, or an anatomical model, of a skull, and wherein the second rigid data comprises an initial 3D reconstruction, or an anatomical model, of a jaw (mandible).

According to a second aspect, there is provided a method for tomographic X-Ray image reconstruction. The method comprises:
  a) acquiring, from an input projection image sequence, first and second 2D X-Ray projection data acquired, respectively at first and second acquisition times of a region of interest of a patient;
  b) providing (i) first 3D rigid object data of, or approximating, a first rigid object in a region of interest of a patient, and (ii) second 3D rigid object data of, or approximating, a second rigid object in a region of interest of a patient;
  c) generating a first registration of the first and/or second 3D rigid object data to the first 2D X-Ray projection data;
  d) generating a second registration of the first and/or second 3D rigid object data to the second 2D X-Ray projection data;
  e) estimating the relative motion of the second rigid object relative to the first rigid object occurring between the first and second acquisition times, and providing a relative motion vector field defining the estimated motion of the second rigid object relative to the first rigid object based on the first and second registrations;
  f) generating corrected 2D X-Ray projection data using the relative motion vector field to correct for the motion of the second rigid object relative to the first rigid object during acquisition of the input projection image sequence; and
  g) generating motion-compensated 3D reconstruction data of the input projection image sequence based on the corrected 2D X-Ray projection data.

According to a third aspect, there is provided an X-Ray imaging system comprising:
  an X-Ray source;
  an X-Ray detector; and
  an apparatus for tomographic X-Ray image reconstruction according to the first aspect or its embodiments.

The X-Ray source is configured to sequentially illuminate a region of interest with X-Ray radiation from a first plurality of acquisition angles.

The X-Ray detector is configured to receive the X-Ray radiation having propagated via the region of interest from a second plurality of acquisition angles to form an input projection image sequence comprising first and second 2D X-Ray projection data acquired, respectively at first and second acquisition times of a region of interest of a patient.

The apparatus for tomographic X-Ray image reconstruction is configured to receive the first and second 2D X-Ray projection data from the X-Ray detector and to generate motion-compensated 3D reconstruction data of the input projection image sequence based on the corrected 2D X-Ray projection data.

Optionally, the X-Ray imaging system is a C-arm imaging system.

Optionally, the 2D X-Ray projection data comprises 2D X-Ray projection data having a pre-applied trajectory correction.

According to a fourth aspect, there is provided a computer program element for controlling a processing unit and/or system of the first and/or third aspect, which, when the computer program element is executed by the processor and/or system, is adapted to perform the method of the second aspect.

According to a fifth aspect, there is provided a computer readable medium having stored the computer program element of the fourth aspect.

In the following application, the term "tomographic X-Ray image reconstruction" refers to an image processing algorithm taking as an input a sequence of 2D X-Ray projection images of a region of interest of a patient obtained, for example, from C-arm. A 3D image of the region of interest of a patient is reconstructed by applying algorithms such as filtered back projection or iterative reconstruction to the input sequence of 2D X-Ray projection images. Thus, "2D X-Ray projection data" is obtained using an acquisition approach such as "cone beam CT" in which a divergent two-dimensional X-Ray beam is directed through a region of interest of a patient towards a two-dimensional X-Ray detector.

In the following application, "2D X-Ray projection data" refers at least to the received pixel values (tracking X-ray intensity and/or energy) from the X-ray detector, as affected by the acquisition system geometry, the source, detector and/or iso-center position and orientation, the patient and or table position and orientation, the time of image acquisition, or any related parameters of the image acquisition.

In the following application, the term "3D rigid object data" refers to a portion of a 3D image defining a rigid body having a deformation which is zero or very small. For the purposes of this application, the term principally refers to bone structures in a patient and/or rigid implants made, for example, of metal. Thus even though the position of a rigid object may move in the 3D image relative to another rigid object (such as a mandible moving with respect to a neurocranial region) the dimensions and shape of the rigid object does not change substantially.

In the following application, the "3D rigid object data" may be of a previously or currently imaged object. However, the "3D rigid object data" may also "approximate" a previously or currently imaged object. For example, the human mandible shares many common aspects across a population of patients. Thus, a computer model of a rigid object such as a mandible could optionally be used to "approximate" a target object.

In the following application, the term "registration" refers at least to a process of aligning a 2D X-Ray projection image of a region of interest of a patient with a projection of a 3D image of the region of interest of the patient, or a model approximating the region of interest of the patient. The skilled person will appreciate that many different registration algorithms can be applied, but the effect is to project through a structure in the 3D image into the plane of the 2D X-Ray projection image. A first match between a projected structure in the projected 2D image and the same structure in the 2D X-Ray projection image can be made. Fine adjustments to the projection angle enable an error between the position of a structure in the 3D image and in the 2D X-Ray projection image to be identified, and for the alignment to be improved.

In the following application, the term "corrected 2D X-Ray projection data" refers to one, or sequence, of 2D X-Ray projection images in which the corresponding acquisition geometry has been modified to correct the position and orientation of the imaging system and all its elements, relative to the imaged object at the time point of the image acquisition.

The term "corrected 2D X-Ray projection data" may also refer to one, or a sequence, of 2D X-Ray projection images in which a subset of pixels have been adjusted in position, intensity, texture, or otherwise to compensate for the motion of a 3D rigid object during the acquisition time of the sequence.

In general the term "corrected 2D X-Ray projection data" may refer to 2D X-Ray projection data that has been adjusted to improve the consistency between the 2D data and the corresponding reconstructed 3D data.

In the following application, the term "motion-compensated 3D reconstruction data" refers to an improved 3D image of the region of interest of the patient having fewer artefacts, as a result of the 3D reconstruction having been performed based upon a sequence of improved 2D X-Ray projection images of the region of interest. An example of an improvement applied to the 2D X-Ray projection images is to adjust the image acquisition geometry of the 2D X-Ray projection images which due to object motion may falsely represent the relative spatial relation between the object and the imaging system, or to move structures appearing in the 2D X-Ray projection images which are in the wrong place as a result of patient motion (such as jaw motion) during an acquisition of the sequence of 2D X-Ray projection images.

Accordingly, a basic idea of the present technique is to identify that a rigid body inside a ROI has moved during the acquisition of a 2D X-Ray projection sequence relative to another rigid body. The motion of the rigid body is compensated by providing a corrected 2D X-Ray projection sequence. Reconstruction of the corrected 2D X-Ray projection sequence results in a higher quality 3D image of the region of interest of the patient.

BRIEF DESCRIPTION OF THE DRAWINGS

Exemplary embodiments will be described with reference to the following drawings.

DETAILED DESCRIPTION OF EMBODIMENTS

The reconstruction of 3D images from rotational C-arm acquisitions is often affected by patient motion due to the relatively long acquisition time of C-arm image acquisitions. In turn, patient motion in the acquired projection images taken by the C-arm is transformed into artefacts in the obtained 3D images. For example, a typical C-arm acquisition of a jaw may have a duration of up to 30 seconds. During that time, a patient with an involuntary jaw tremor, for example, may move their jaw up and down, causing blurriness and artefacts that penetrate the significant portion of the reconstructed 3D image. Various motion compensation methods have been developed to address this problem. Deformable motion compensation usually relies on the motion estimation of some key features, and the corresponding interpolation of a continuous motion vector field. However, rigid motion compensation is often applied to images of bone structures, such as the skull.

However a conventional application of rigid motion compensation to the skull cannot compensate for jaw motion. In rigid motion compensation, there is an assumption of a single, fully rigid object in the reconstructed volume. This assumption is violated in the case of the motion of the human jaw. Although this application discusses a solution to the foregoing problem in terms of relationship between the neurocranium and the mandible (jaw), it is also clear that there are many other imaging scenarios in which the same problem presents itself. For example, obtaining 3D images of a hip area, of the knee joint, an elbow joint, or an ankle joint are some other examples of images in which at least two rigid objects are present in a region of interest and where rigid motion compensation may not conventionally be possible because the assumption that the region of interest contains only one rigid object is violated, and the described technique is applicable to at least these cases.

Accordingly, it is generally proposed to solve this problem by applying rigid motion compensation separately to two separate and distinct rigid image regions in the region of interest. For example, the neurocranium and the mandible may be considered, respectively, to be first and second rigid objects in a region of interest.

Figure 1:
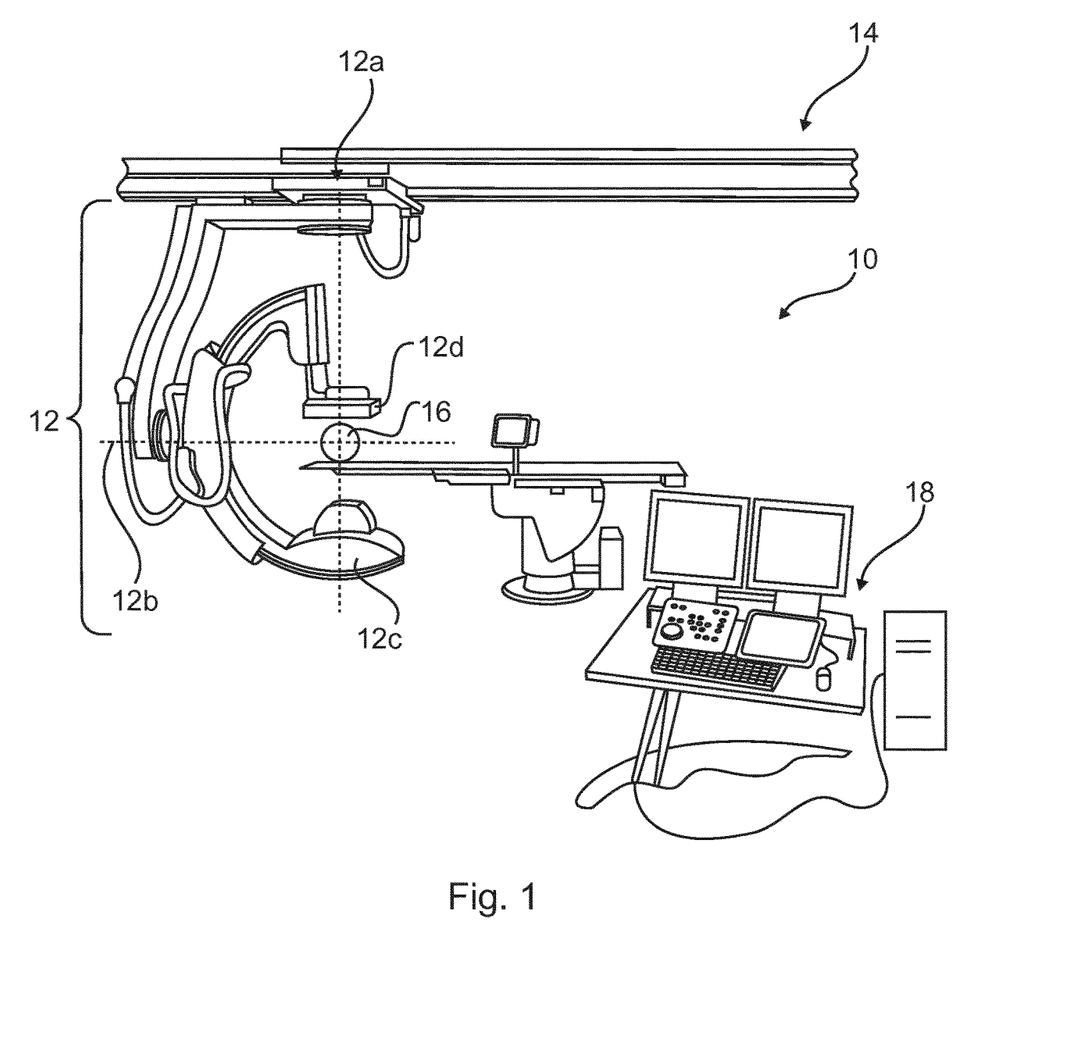
FIG. 1 illustrates a C-arm X-Ray image acquisition system.

FIG. 1 illustrates a C-arm acquisition suite 10 (X-Ray imaging system). It is noted that although the C-arm acquisition system, applying the "cone beam computed tomography" technique (CBCT), is a common 3D image acquisition technique, the image acquisition technique is not limited to this acquisition technique.

The C-arm acquisition suite 10 comprises a C-arm 12 attached to the ceiling 14 of the C-arm acquisition suite. The C-arm 12 is attached to the ceiling 14 by a rotatable azimuthal connection 12a, with a rotatable bearing 12b providing a degree of freedom in the inclination direction. An X-Ray source 12c is positioned on a first end of the C-arm 12, facing an X-Ray detector 12d (optionally a digital flat panel detector). An examination area 16 is provided in between the X-Ray source 12c and the X-Ray flat panel detector 12d. Dependent upon the angulation of the X-Ray source 12c and the X-Ray detector 12d with respect to an object (such as a patient's head) in the examination area 16, a sequence of 2D X-Ray projection images may be obtained as the C-arm 12 is moved in an orbit around the examination area 16. The sequence of 2D X-Ray projection images is provided to an apparatus 18 configured to apply a tomographic reconstruction algorithm to the 2D X-Ray projection image sequence, and thus to provide and optionally display a 3D image of the region of interest of a patient in the examination area 16. Typically, the apparatus 18 applies a filtered back projection algorithm, or an iterative reconstruction algorithm to obtain the 3D image of the region of interest of the patient, although many other such tomographic reconstruction algorithms may also be applied.

Figure 2:
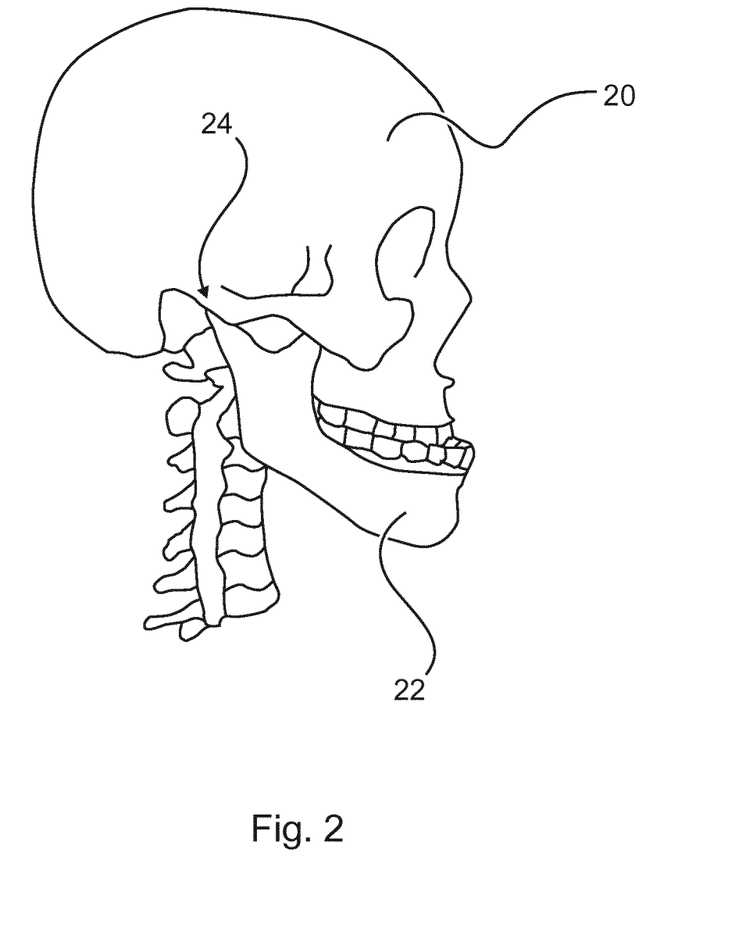
FIG. 2 illustrates a lateral view of a human skull.

FIG. 2 illustrates a lateral view of a human head. Although the human head is comprised of many interlocking bone structures, it is sufficient for this application to consider that the interlocking network of bones forming the neurocranium 20 forms a first rigid structure, and the mandible 22 forms a second rigid structure. The mandible 22 is connected to the neurocranium 20 via the temporomandibular joint 24. It may be considered that the first rigid object (neurocranium 20) has a first frame of reference, and that the second rigid object (mandible 22) has a second frame of reference. These may be aligned with each other, or progressively become angled away from each other, as the second rigid object 22 moves in relation to the first rigid object 20.

Figure 3:
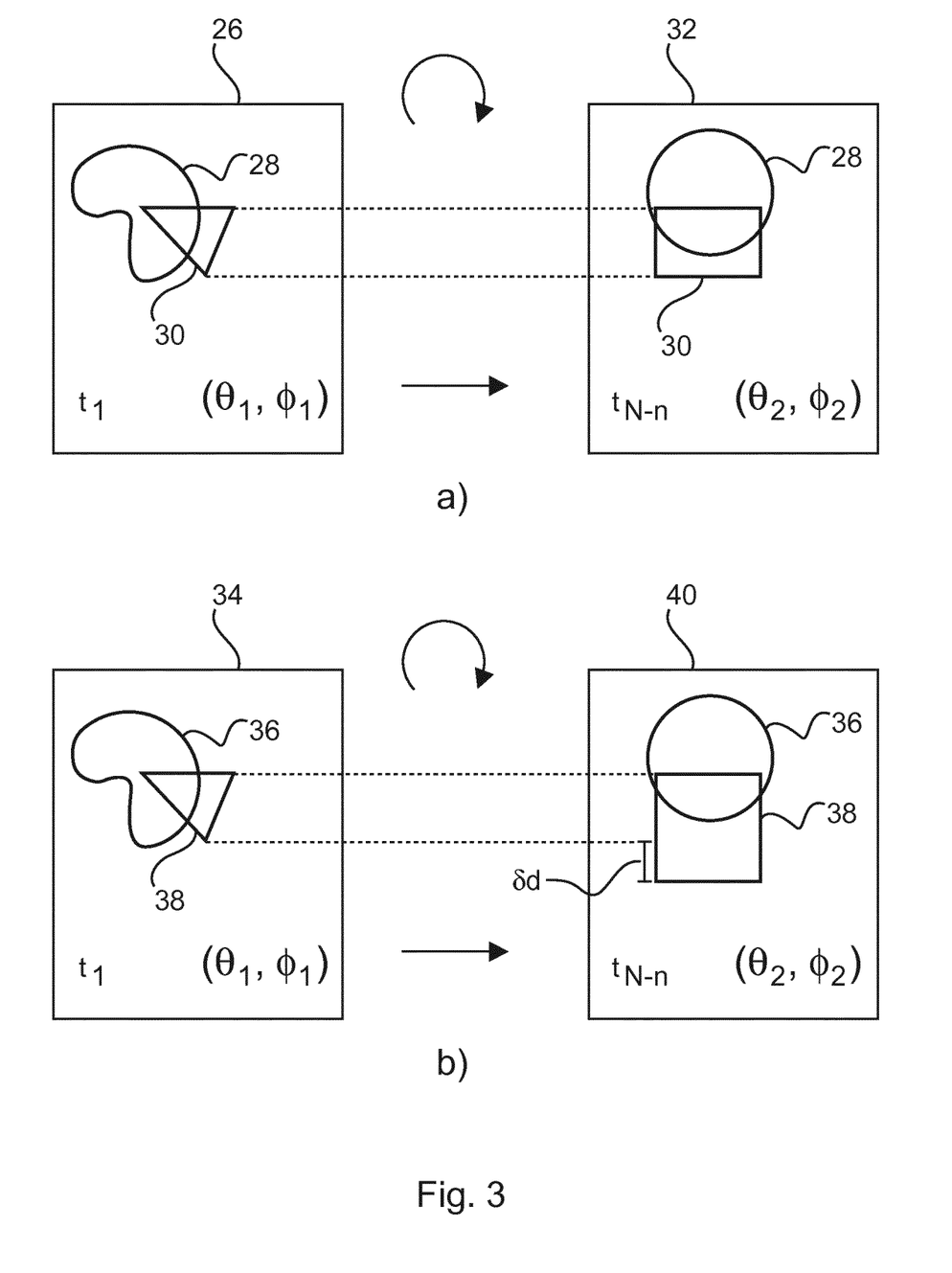
FIG. 3 illustrates examples of perfect and imperfect 2D projection sequence image acquisition.

FIG. 3a) illustrates a schematic of two frames taken from a sequence of 2D X-Ray projection images as may be obtained using, for example, a C-arm. A first frame 26 obtained at time $t_1$ with a C-arm geometry angled at $\theta_1$, $\varphi_1$ provides a projection of a lateral view of a neurocranium 28 and a mandible 30 (which are, for clarity, illustrated throughout in a schematic manner and are not anatomically accurate). At time $t_1$, mandible 30 is raised. The C-arm system then advances its orbit at time $t_{N-n}$, although no motion of the mandible 30 with respect to the neurocranium 28 occurs. Thus, the second frame 32 obtained at time $t_{N-n}$ and with a C-arm geometry angled at $\theta_2$, $\varphi_2$ provides a projection of a front view of the neurocranium 28 and a mandible 30. No patient motion has occurred, and thus the mandible 30 is at the same position with respect to the neurocranium 28 as in the first frame 26. Providing the first 26 and second 32 frames to a tomographic reconstruction algorithm will not result in artefacts in the mandible region of the frame.

FIG. 3b) illustrates the case when a third 2D X-Ray projection frame 34 comprising a similar neurocranium 36 and mandible 38 is captured at a time $t_1$ with a C-arm geometry angled at $\theta_1$, $\varphi_1$. In the time duration until the acquisition of fourth 2D X-Ray projection frame 40 at time $t_2$, the mandible 38 has dropped by a distance 5d. Using the third and fourth X-Ray projection frames to reconstruct a 3D tomographic image will result in blurriness and artefacts.

Accordingly, it has been identified by the present inventors that an initial 3D model can be used (either of patient, or of an idealized 3D model) to provide 2D projection images for comparison to 2D projection images acquired when the patient has moved, and to correct position of the rigid objects in the 2D images, enabling a more accurate subsequent 3D image to be reconstructed.

According to a second aspect, there is provided a tomographic image reconstruction method, comprising:
 a) acquiring, from an input projection image sequence, first and second 2D X-Ray projection data acquired, respectively at first and second acquisition times of a region of interest of a patient;
 b) providing (i) first 3D rigid object data of, or approximating, a first rigid object in a region of interest of a patient, and (ii) second 3D rigid object data of, or approximating, a second rigid object in a region of interest of a patient;
 c) generating a first registration of the first and/or second 3D rigid object data to the first 2D X-Ray projection data;
 d) generating a second registration of the first and/or second 3D rigid object data to the second 2D X-Ray projection data;
 e) estimating the relative motion of the second rigid object relative to the first rigid object occurring between the first and second acquisition times, and providing a relative motion vector field defining the estimated motion of the second rigid object relative to the first rigid object based on the first and second registrations;
 f) generating corrected 2D X-Ray projection data using the relative motion vector field to correct for the motion of the second rigid object relative to the first rigid object during acquisition of the input projection image sequence; and
 g) generating motion-compensated 3D reconstruction data of the input projection image sequence based on the corrected 2D X-Ray projection data.

Figure 4:
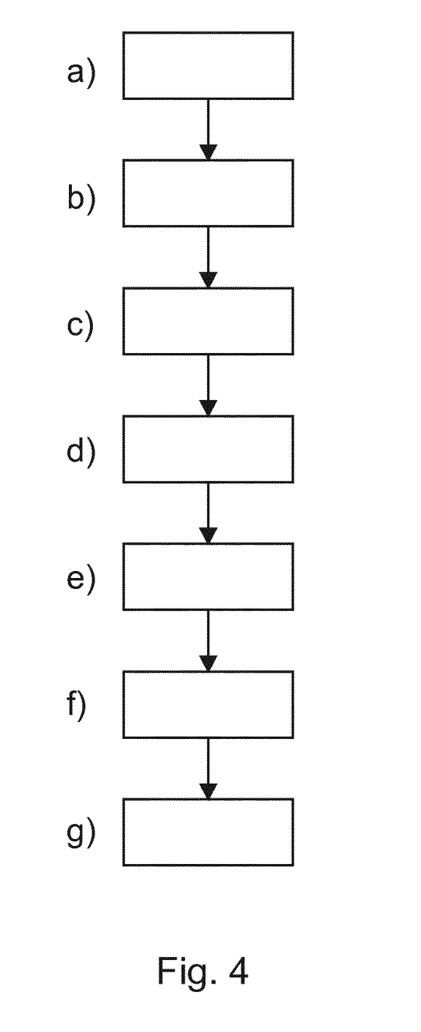
FIG. 4 illustrates a method according to the second aspect.

FIG. 4 illustrates the method according to the second aspect.

In step a), the first and second 2D X-Ray projection data are optionally acquired by a C-arm using the cone beam computed tomography (CBCT) protocol. Provided raw 2D X-Ray projection sequences are retained from image acquisitions, for example from an archival facility or a PACS system, the algorithm can be applied, for example, to previously-acquired CBCT data. Optionally, the input projection image sequence is acquired from C-arm completing an orbit (optionally a rotational orbit) around the region of interest. It should be noted that the acquisition of the first and second projection images at first and second acquisition times this implies that the first and second projection images are acquired at different orientations relative to the region of interest.

In step b), the provision of first and second 3D rigid object data of first and second rigid objects in the region of interest optionally arises as a result of an initial reconstruction being performed on the input projection image sequence. In some cases, although movement of the first and/or second rigid object during the acquisition of the input projection image sequence may cause some image artefacts and/or blurring, it may still be possible to distinguish first and second 3D rigid object data in a reconstructed 3D image. The first 3D rigid object data and the second 3D rigid object data may be obtained, for example, by segmenting the reconstructed 3D image.

Optionally, first and second 3D rigid object data may be provided from generic model data of the region of interest. For example, the neurocranium and the mandible have a relatively predictable shape across a large proportion of the population, which will approximate but not necessarily exactly match these bones in a patient. However, the first and second 3D rigid object data may be provided from an anatomical model data database as a priori initial information.

Optionally, the first 3D rigid object data may be provided from a reconstruction of the input projection image sequence, and the second 3D rigid object data may be provided from an anatomical model database. This composite approach to providing the initial information might be attractive in a situation where artefacts grossly obscure the mandible area of a reconstructed initial 3D image, but the neurocranial area of the reconstructed initial 3D image possesses no artefacts. In this case, a segmentation to identify the neurocranial area (first 3D rigid object data) combined with a cutting and stitching of the model of the mandible (second 3D rigid object data) may be performed to generate the initial 3D model.

Having provided the initial 3D model of the region of interest in the ways discussed above, it is possible to use the initial 3D model as a "golden reference" and to compare projections at various angles through it to images of the input projection image sequence. Identifying deviations between temporarily spaced projections of the first 3D rigid data and the second 3D rigid object data enables the relative motion of the second 3D rigid object to the first 3D rigid object to be estimated.

Accordingly, in steps c) and d), such registrations are performed. Optionally, in step c), a first registration of the first 3D rigid object data to the first and/or second 2D X-Ray projection data is provided. Optionally, in step d), a second registration of the second 3D rigid object data to the first and/or second 2D X-Ray projection data is provided.

Figure 5:
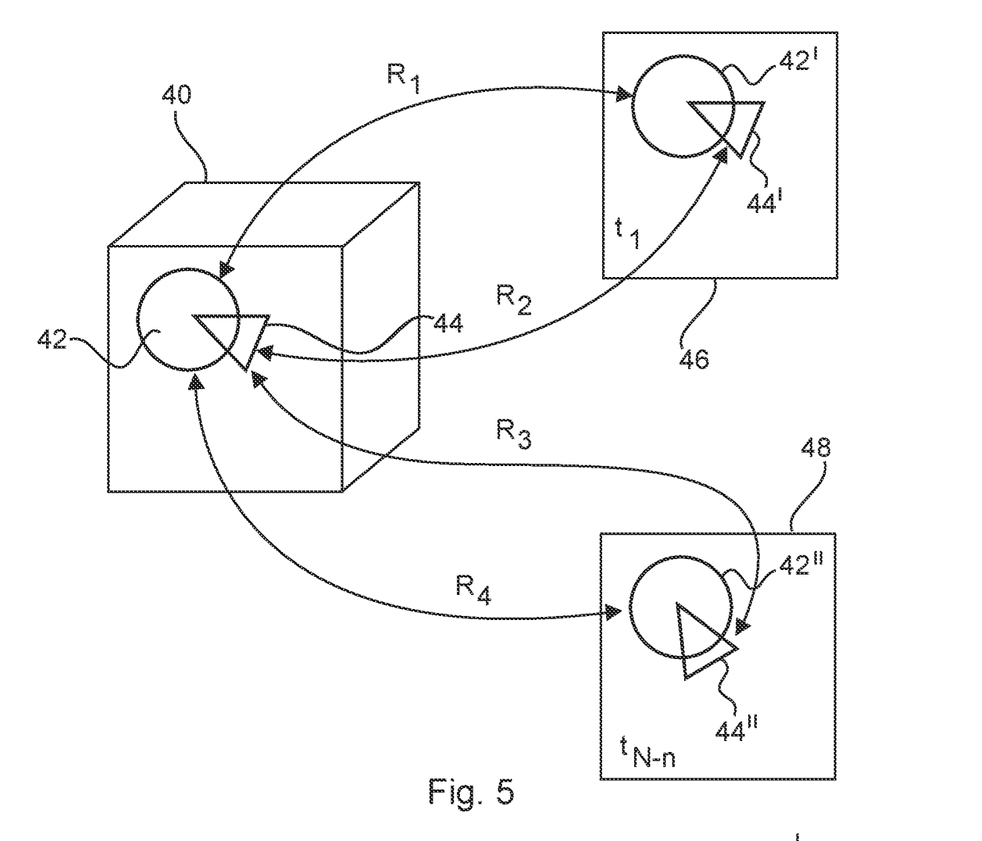
FIG. 5 illustrates examples of registration relationships.

FIG. 5 illustrates the registrations occurring in steps c) and d). A portion of initial 3D object data 40 is provided comprising first 3D rigid object data 42 and second 3D rigid object data 44. In addition, a first 46 and a second 48 image from an input projection image sequence (optionally acquired by C-arm) are provided. The first 2D X-Ray projection data acquired at time $t_1$ comprises a first 2D projection 42' of the first rigid object and a first 2D projection 44' of the second rigid object in the region of interest. The second 2D X-Ray projection data 48 acquired at time $t_{N-n}$, comprises a second 2D projection 42" of the first rigid object and a second 2D projection 44" of the second rigid object. In FIG. 5, the symbol R refers to registration between two objects in a generic coordinate system, for example the Cartesian coordinate system, the polar coordinate system, or many others.

In a complex case, a first rigid object and a second rigid object will experience a relative motion during the acquisition of the input projection image sequence. Additionally, the first rigid object and second rigid object may experience a common-mode motion during the acquisition of the input projection image sequence. In the example of a neurocranium and mandible, motion of the spine, a displacement of the entire head caused by a swaying of the patient on their feet would introduce such a common-mode motion to both the first and second rigid objects. In a case where a common-mode component exists, it is necessary to identify this using at least four registrations and then to cancel the common-mode motion between the first and second rigid objects to reveal the relative motion between the first and second rigid objects. Accordingly, this complex case is illustrated in FIG. 5 with four registrations. However, it is emphasized that acquiring and performing four registrations is not essential the definition of the invention because if the first and second rigid objects experience no, or negligible common-mode motion (in practice, if a patient is able to stand or lie relatively still during the image acquisition, or if the patient is lying down on an examination table, for example), only two registrations need to be performed to determine the motion of the second rigid object over time relative the first rigid object.

The first 3D rigid object data 42 may be registered to a first 2D projection 42' of the first rigid object in a first registration $R_1$.

The second 3D rigid object data 44 may be registered to a first 2D projection 44' of the second rigid object in a second registration $R_2$.

The second 3D rigid object data 44 may be registered to a second 2D projection 44" of the first rigid object in a third registration $R_3$.

The first 3D rigid object data 42 may be registered to a second 2D projection 42" of the first rigid object in a fourth registration $R_4$.

Common mode motion of the first rigid object 42 in between capture times $t_1$ and $t_2$ may be given (in any appropriate coordinate system) by identifying a common component of $R_4-R_1$, and $R_3-R_2$.

In the simplest case, no common mode motion exists (in other words, first 2D projection 42' and the second 2D projection 42" are assumed at the same position in both frames) and only the motion of second 3D rigid object relative to the first 3D rigid object between times $t_1$ and $t_{N-n}$, needs to be identified. Alternatively, common mode motion may be removed by subtraction once its components have been identified.

Thus, in step e), the relative motion of the second rigid object relative to the first rigid object occurring between the first and second acquisition times is found by calculating $R_3-R_2$ (assuming an identical coordinate system between the first and second 2D X-Ray projection data).

Typically, the motion of the first and the second rigid object may be translated in a first and a second modified trajectory of the C-arm system. From the two modified trajectories a first and a second motion compensated 3D reconstruction is generated where the first reconstruction would provide an artefact reduced reconstruction of the first object and the second reconstruction would provide an artefact reduced reconstruction of the second object.

Optionally, in a simple case, steps c) and d) comprise:
c) generating a first registration of the first 3D rigid object data to the first 2D X-Ray projection data;
d) generating a second registration of the second 3D rigid object data to the second 2D X-Ray projection data.

Figure 6:
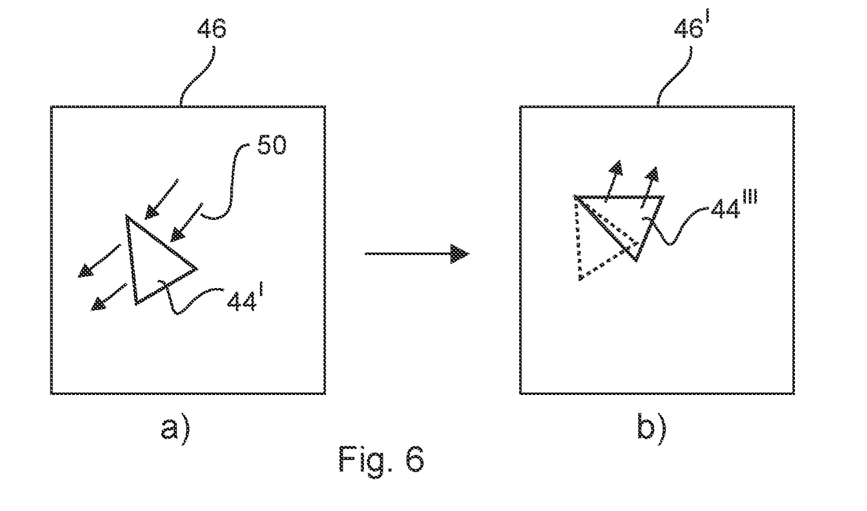
FIG. 6 illustrates an example of motion vector field identification.

FIG. 6a) illustrates first 2D X-Ray projection data 46, in which the first 2D projection 44' of the second rigid object (such as a mandible) is associated with an estimated relative motion field illustrated by the arrows 50.

FIG. 6b) illustrates a frame of corrected first 2D X-Ray projection data 46', in which the relative motion vector field 50 computed in step e) is applied to correct for the motion of the second rigid object between the first and second acquisition time, to thus generate a corrected 2D projection 44''' of the second rigid object in step f).

In step g), a forward back-projection, iterative reconstruction algorithm, or other 3D image reconstruction algorithm is applied to the corrected 2D X-Ray projection data. It will be appreciated that although the present example has explained the algorithm in terms of two frames of an input projection image sequence, the algorithm may be applied to an arbitrarily large number of input projection images (2D X-Ray projection data).

Conceivably, a patient may move in the region of interest for less than the total acquisition time of the input projection image sequence.

Thus, a sliding window may be applied to successive frames of the input projection image sequence. For the frames within the sliding window, an assessment of the relative motion of the second rigid object relative to the first rigid object may be provided, and corrected 2D X-Ray projection data may be calculated for frames within the sliding window. In this way, relative motion between the first and second rigid object may be compensated but the algorithm does not need to be applied to all frames of the input projection image sequence, saving computational effort.

Optionally, the first and/or second 3D rigid object data is acquired from (i) an initial 3D reconstruction of the input projection image sequence, or (ii) a prior 3D imaging scan of the region of interest of the patient.

Optionally, the first and/or second 3D rigid object data is acquired from a database of anatomical models.

Optionally, a database of anatomical models or anonymized example patient models (for example of neurocranial bone shapes, mandible shapes, and the like) may be provided on a secure external server. The first and/or second 3D rigid object data may be provided from such a database. This means that an initial 3D reconstruction used in the algorithm is more accurate.

It will be appreciated that the computational complexity of the registration process may be reduced if the search space of registrations between the 3D rigid object data, and the first and second 2D X-Ray projection data is reduced. An effective way of reducing the search space is to exploit anatomical limitations to the motion of the first and second 3D rigid objects. As one example, the temporomandibular joint restricts the motion of the mandible relative to the neurocranium into a sector of the 3D rigid object data defined by an arc enclosing 50° vertical and 20° horizontal, for example. Accordingly, this sector is one example of a motion model prior of the second rigid object relative to the first rigid object.

Therefore, optionally there are provided the steps:
- b1) providing a motion model prior of the first and/or second rigid object, wherein the motion model prior defines a subset of a total set of possible motion trajectories of the first and/or second rigid object; and
- e1) estimating the relative motion of the second rigid object relative to the first rigid object using, at least in part, the motion model prior to restrict the possible number of motion trajectories of the second rigid object considered in the estimate.

Optionally, the motion model prior is a simulation of a flexible joint between the first and second rigid objects.

Optionally, the motion model prior is a simulation of the temporomandibular joint.

Optionally, the first registration and/or the second registration of the first and/or second 3D rigid object data is restricted by the condition that an overlap in 3D space in the motion-compensated 3D reconstruction data of the first 3D rigid object data and the second 3D rigid object data is not permissible.

In one optional registration approach, generating the first registration further comprises:
- c1) providing forward projection data of the first 3D rigid object data;
- c2) generating a similarity metric representing the similarity of the forward projection data to the first X-ray projection data; and
- c3) registering the first rigid object in the first 3D anatomical data to the first X-ray projection data using the similarity metric.

An example of a similarity metric is the normalized 2D cross-correlation between the same object in the forward projection data and the first or second X-ray projection data. Many other similarity metrics may be generated and applied.

Optionally, estimating the relative motion of the second rigid object relative to the first rigid object occurring between the first and second acquisition times further comprises:
- e2) identifying a first rigid motion curve of the second rigid object by comparing a subsequent position of the second rigid object in the second 2D X-Ray projection data to an initial position of the second rigid object in the first 2D X-Ray projection data.

Optionally, estimating the motion of the first rigid object relative to the second rigid object further comprises:
- e3) defining a spatially intermediate portion of the first and/or second 2D X-Ray projection data in-between the first and second rigid objects;
- e4) identifying a second rigid motion curve of the first rigid object in the spatially intermediate portion by comparing a subsequent position of the first rigid object in the second 2D X-Ray projection data as compared to an initial position of the first rigid object in the first 2D X-Ray projection data;
- e5) generating a rigid composite motion curve as a combination of the first and second rigid motion curves.

Optionally, the corrected 2D X-Ray projection data is generated based exclusively upon the motion vector field of the second rigid anatomical data.

Optionally, estimating the absolute motion of the first rigid object and the second rigid object relative to the imaging geometry, and providing an absolute motion vector field defining the estimated motion of the first and second rigid objects relative to the imaging geometry; and
- f1) generating the corrected 2D X-Ray projection data additionally using the absolute motion vector field combined with the relative motion vector field.

Optionally, there is the step of:
- h) displaying the motion-compensated 3D reconstruction data to a user.

Optionally, the first rigid anatomical data comprises an initial 3D reconstruction, or an anatomical model, of a skull, and wherein the second rigid anatomical data comprises an initial 3D reconstruction, or an anatomical model, of a jaw.

A basic explanation of the steps is that:
1) an initial reconstruction of a 3D model of a first rigid object (lower jaw), and the corresponding model of a second rigid object (neurocranium) is created from the rotational projection sequence or is read from a model database. It is also possible to combine the initial reconstruction of the second rigid object with a 3D model of the first rigid object. In many cases, the use of a 3D model of the lower jaw may be necessary since the initial construction of the lower jaw region may not be sufficiently accurate owing to patient-induced relative motion between the first and second rigid objects.
2) the first and second rigid objects are registered to each individual 2D projection of the rotational sequence using a suitable similarity metric (such as a forward projection of the model, and a normalized 2D cross correlation).
3) A motion vector field is calculated based on the estimated motion of the first and second rigid objects. The local motion vectors are calculated thereby from one of two of the rigid object motion curves, depending on the 3D distance to the object.

Optionally, two dedicated 3D regions may be defined in which the motion information from the two objects are used separately. In an intermediate region between the first and second objects, motion vectors may be calculated based on a combination of the two rigid motion curves.

Optionally, the motion of the main part of the first rigid object may be translated into a modified trajectory of the C-arm system while the motion of the second rigid object remains the only relative motion vector field for motion compensated reconstruction from an arbitrary trajectory. In this case, interpolation of motion vector field would not then be required.

The two reconstructions may then be combined into a unified motion compensated 3D reconstruction by using from the first motion compensated 3D reconstruction the spatial regions corresponding to the first object and using from the second motion compensated 3D reconstruction the spatial regions corresponding to the second object. Optionally intermediate spatial locations may be interpolated, or extracted from any number of further motion compensated reconstructions based on intermediate modified trajectories of the C-arm system, or based on intermediate or interpolated motion vector fields.

4) A motion-compensated 3D reconstruction is calculated based on the motion vector field and/or based on modified trajectories of the imaging system.

Optionally, during the 2D/3D registration, the two rigid structures may be connected by a flexible joint with similar freedom to the temporomandibular joint. This reduces the degrees of freedom for the 2D/3D registration and therefore improves robustness, speed, and accuracy of the algorithm, without limiting its general applicability.

Optionally, additional constraints may be implemented for the relative motion of the two rigid structures. An overlap in 3D space of structures may be restricted.

Optionally, instead of a projection-based registration, an image-artefact feature-based motion compensation may be performed using the two rigid structures. In this case, the image artefact feature (such as entropy) in the image volume is minimized by optimizing the rigid motion parameters of the first and second rigid objects.

Figure 7:
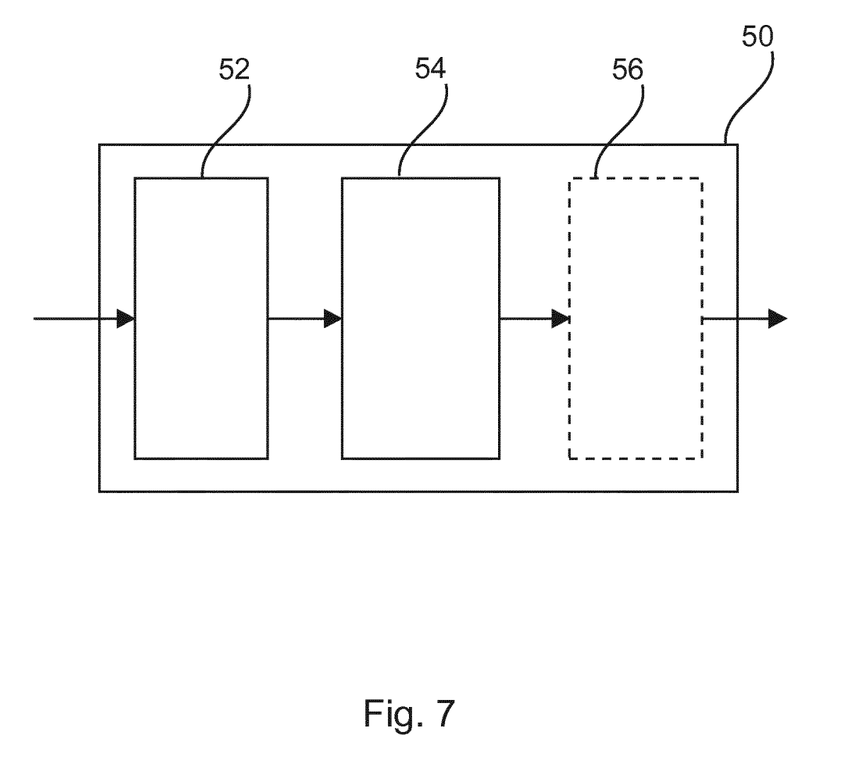
FIG. 7 illustrates an apparatus according to the first aspect.

According to a first aspect of the invention, there is provided an apparatus 50 for tomographic image reconstruction. The apparatus comprises:

an input unit 52; and a processing unit 54.

The input unit is configured to acquire, from an input projection image sequence, first and second 2D X-Ray projection data of a region of interest of an object acquired, respectively at first and second acquisition times, and the input unit is configured to provide (i) first 3D rigid object data of, or approximating, a first rigid object in a region of interest of a patient, and (ii) second 3D rigid object data of, or approximating, a second rigid object in a region of interest of a patient.

The processing unit is configured to generate a first registration of the first and/or second 3D rigid object data to the first 2D X-Ray projection data, to generate a second registration of the first and/or second 3D rigid object data to the second 2D X-Ray projection data, to estimate the relative motion of the second rigid object relative to the first rigid object occurring between the first and second acquisition times, and providing a relative motion vector field defining the estimated motion of the second rigid object relative to the first rigid object based on the first and second registrations, to generate corrected 2D X-Ray projection data using the relative motion vector field to correct for the motion of the second rigid object relative to the first rigid object during acquisition of the input projection image sequence, and to generate motion-compensated 3D reconstruction data of the input projection image sequence based on the corrected 2D X-Ray projection data.

Optionally, the apparatus comprises an output unit 56 for displaying the motion-compensated 3D reconstruction to a user. For example, the output unit 56 may be a computer display. Of course, the output unit could be a data communication means configured to transmit the motion-compensated 3D reconstruction to another computer or display unit. Optionally, the motion-compensated 3D reconstruction can be securely transmitted to a hand-held display or provided to a secure data storage means such as a PACS server.

FIG. 7 illustrates an apparatus 50 in accordance with the first aspect and its optional embodiments.

Optionally, the apparatus is provided as a computer (optionally configured with a graphics processing unit), as function-specific hardware amended, for example, in a field programmable gate array (FPGA) or an application-specific integrated circuit (ASIC). Alternatively, the apparatus can be provided on a centralized server in a PACS system, for example. The input unit 52 is configured to receive input projection image sequences, and first and second 3D rigid object data. However, the skilled person will appreciate the wide range of devices can function to receive such data. For example, the input unit can comprise a connection to an X-Ray tomography or C-arm acquisition system. Optionally, the input unit can comprise a Modem, a LAN or WAN connection, or another data communication means. Optionally, the apparatus 50 may comprise an output unit 56. The output unit can, for example, be a graphics display card to enable the display of motion-compensated 3D reconstruction data on a computer monitor. Optionally, the output unit can, for example, comprise a data communication means enabling motion-compensated 3D reconstruction data to be communicated over a secure LAN, WAN, or written to a CD-ROM, DVD-ROM, USB drive, a portable hard-drive, a portable tape-drive or similar.

Optionally, the apparatus may comprise at least the embodiments of the first aspect discussed in the "summary of the invention" section.

According to a third aspect, there is provided an X-Ray imaging system 10. The system comprises:

an X-Ray source 12c;

an X-Ray detector 12d; and an apparatus 18 for tomographic X-Ray image reconstruction according to the first aspect all of its embodiments.

The X-Ray source 12c is configured to sequentially illuminate a region of interest 16 with X-Ray radiation from a first plurality of acquisition angles.

The X-Ray detector 12d is configured to receive the X-Ray radiation having propagated via the region of interest 16 from a second plurality of acquisition angles to form an input projection image sequence comprising first and second 2D X-Ray projection data acquired, respectively at first and second acquisition times of a region of interest of a patient.

The apparatus for tomographic X-Ray image reconstruction 18 is configured to receive the first and second 2D X-Ray projection data from the X-Ray detector 12d and to generate motion-compensated 3D reconstruction data of the input projection image sequence based on the corrected 2D X-Ray projection data.

According to a fourth aspect, there is provided a computer program element for controlling a processing unit and/or system of the first and/or third aspect, which, when the computer program element is executed by the processor and/or system, is adapted to perform the method of the second aspect.

According to a fifth aspect, there is provided a computer readable medium having stored the computer program element of the fourth aspect.

A computer program element might therefore be stored on a computer unit, which might also be an embodiment of the present invention. This computing unit may be adapted to perform or induce performance of the steps of the method described above.

Moreover, it may be adapted to operate the components of the above-described apparatus.

The computing unit can be adapted to operate automatically and/or execute orders of a user. A computer program may be loaded into the working memory of a data processor. The data processor may thus be equipped to carry out the method of the invention.

This exemplary embodiment of the invention covers both the computer program that has the invention installed from the beginning, and a computer program that by means of an update turns an existing program into a program that uses the invention. A computer program may be stored and/or distributed on a suitable medium, such as an optical storage medium, or a solid state medium supplied together with, or as part of other hardware, but may also be distributed in other forms, such as via the Internet or other wired or wireless telecommunication systems.

However, the computer program may also be presented over a network like the World Wide Web, and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It should to be noted that embodiments of the invention are described with reference to different subject-matters. In particular, some embodiments are described with reference to method-type claims, whereas other embodiments are described with reference to device-type claims. However, a person skilled in the art will gather from the above, and the following description that, unless otherwise notified, in addition to any combination of features belonging to one type of subject-matter, other combination between features relating to different subject-matters is considered to be disclosed with this application.

All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An apparatus for tomographic X-Ray image reconstruction, the apparatus comprising:
    input circuitry configured to:
        acquire, from an input projection image sequence, first 2D X-Ray projection data and second 2D X-Ray projection data of a region of interest of an object acquired, respectively, at first and second acquisition times, and
        provide (i) first 3D rigid object data of, or approximating, a first rigid object in a region of interest of a patient, and (ii) second 3D rigid object data of, or approximating, a second rigid object in a region of interest of the patient; and
    a processor configured to:
        generate a first registration of at least one of the first 3D rigid object data and the second 3D rigid object data to the first 2D X-Ray projection data,
        generate a second registration of at least one of the first 3D rigid object data and the second 3D rigid object data to the second 2D X-Ray projection data,
        estimate a relative motion of the second rigid object relative to the first rigid object occurring between the first and second acquisition times,
        provide a relative motion vector field defining the relative estimated motion of the second rigid object relative to the first rigid object based on the first registration and the second registration,
        generate corrected 2D X-Ray projection data using the relative motion vector field to correct for the relative motion of the second rigid object relative to the first rigid object during acquisition of the input projection image sequence, and
        generate motion-compensated 3D reconstruction data of the input projection image sequence based on the corrected 2D X-Ray projection data.

2. The apparatus for tomographic X-Ray image reconstruction of claim 1:
    wherein at least one of the first 3D rigid object data and the second 3D rigid object data is acquired by the input circuitry from (i) an initial 3D reconstruction of the input projection image sequence, or (ii) a prior 3D imaging scan of a region of interest of the patient.

3. The apparatus for tomographic X-Ray image reconstruction of claim claim 1,
    wherein at least one of the first 3D rigid object data and the second 3D rigid object data is acquired by the input circuitry from a database of anatomical models.

4. The apparatus for tomographic X-Ray image reconstruction of claim 1,
    wherein the input circuitry is configured to provide a motion model prior of at least one of the first rigid object and the second rigid object, wherein the motion model prior defines a subset of a total set of possible motion trajectories of at least one of the first rigid object and the second rigid object; and
    wherein the processor is further configured to estimate the relative motion of the second rigid object relative to the first rigid object using, at least in part, the motion model prior to restrict the possible number of motion trajectories of the second rigid object considered in the estimate.

5. The apparatus for tomographic X-Ray image reconstruction of claim 1,
    wherein the processor is further configured to generate the first registration by providing forward projection data of the first 3D rigid object data, generating a similarity metric representing the similarity of the forward projection data to the first 2D X-Ray projection data, and registering the first rigid object in first 3D anatomical data to the first 2D X-Ray projection data using the similarity metric.

6. The apparatus for tomographic X-Ray image reconstruction of claim 1,
    wherein estimating the relative motion of the second rigid object relative to the first rigid object occurring between the first and second acquisition times further comprises:
    identifying a first rigid motion curve of the second rigid object by comparing a subsequent position of the second rigid object in the second 2D X-Ray projection data to an initial position of the second rigid object in the first 2D X-Ray projection data.

7. The apparatus for tomographic X-Ray image reconstruction of claim 6,
    wherein the processor is further configured to estimate the relative motion of the first rigid object relative to the second rigid object by defining a spatially intermediate portion of at least one of the first 2D X-Ray projection data and the second 2D X-Ray projection data in-between the first rigid object and the second rigid object, identifying a second rigid motion curve of the first rigid object in the spatially intermediate portion by comparing a subsequent position of the first rigid object in the second 2D X-Ray projection data as compared to an initial position of the first rigid object in the first 2D X-Ray projection data, and generating a rigid composite motion curve as a combination of the first rigid motion curve and the second rigid motion curve.

8. The apparatus for tomographic X-Ray image reconstruction of claim 1,
wherein the processor is further configured to correct the 2D X-Ray projection data based upon the relative motion vector field of the second rigid data.

9. The apparatus for tomographic X-Ray image reconstruction of claim 1,
wherein the processor is further configured to estimate an absolute motion of the first rigid object and the second rigid object relative to imaging geometry, provide an absolute motion vector field defining the estimated relative motion of the first rigid object and the second rigid object relative to the imaging geometry, and generate the corrected 2D X-Ray projection data additionally using the absolute motion vector field combined with the relative motion vector field.

10. The apparatus for tomographic X-Ray image reconstruction of claim 1, further comprising:
output circuitry configured to display the motion-compensated 3D reconstruction data to a user.

11. The apparatus for tomographic X-Ray image reconstruction of claim 1,
wherein the first rigid data comprises an initial 3D reconstruction, or an anatomical model, of a skull, and wherein the second rigid data comprises an initial 3D reconstruction, or an anatomical model, of a jaw.

12. A method for tomographic X-Ray image reconstruction, the method comprising:
acquiring, from an input projection image sequence, first 2D X-Ray projection data and second 2D X-Ray projection data acquired, respectively, at first and second acquisition times of a region of interest of a patient;
providing (i) first 3D rigid object data of, or approximating, a first rigid object in a region of interest of the patient, and (ii) second 3D rigid object data of, or approximating, a second rigid object in a region of interest of the patient;
generating a first registration of at least one of the first 3D rigid object data and the second 3D rigid object data to the first 2D X-Ray projection data;
generating a second registration of at least one of the first and the second 3D rigid object data to the second 2D X-Ray projection data;
estimating a relative motion of the second rigid object relative to the first rigid object occurring between the first and second acquisition times;
providing a relative motion vector field defining the estimated relative motion of the second rigid object relative to the first rigid object based on the first registration and the second registration;
generating corrected 2D X-Ray projection data using the relative motion vector field to correct for the relative motion of the second rigid object relative to the first rigid object during acquisition of the input projection image sequence; and
generating motion-compensated 3D reconstruction data of the input projection image sequence based on the corrected 2D X-Ray projection data.

13. An X-Ray imaging system comprising:
an apparatus for tomographic X-Ray image reconstruction according to claim 1; and
an X-Ray source configured to sequentially illuminate a region of interest with X-Ray radiation from a first plurality of acquisition angles;
an X-Ray detector is-configured to receive the X-Ray radiation having propagated via the illuminated region of interest from a second plurality of acquisition angles to form the input projection image sequence comprising the first 2D X-Ray projection data and the second 2D X-Ray projection data acquired, respectively, at the first and second acquisition; and
wherein the apparatus for tomographic X-Ray image reconstruction is configured to receive the first 2D X-Ray projection data and the second 2D X-Ray projection data from the X-Ray detector and to generate the motion-compensated 3D reconstruction data of the input projection image sequence based on the corrected 2D X-Ray projection data.

14. A non-transitory computer-readable medium having stored a computer program comprising instructions which, when executed by a processor, cause the processor to:
acquire, from an input projection image sequence, first 2D X-Ray projection data and second 2D X-Ray projection data of a region of interest of an object acquired, respectively, at first and second acquisition times;
provide (i) first 3D rigid object data of, or approximating, a first rigid object in a region of interest of a patient, and (ii) second 3D rigid object data of, or approximating, a second rigid object in a region of interest of the patient;
generate a first registration of at least one of the first 3D rigid object data and the second 3D rigid object data to the first 2D X-Ray projection data;
generate a second registration of at least one of the first 3D rigid object data and the second 3D rigid object data to the second 2D X-Ray projection data;
estimate a relative motion of the second rigid object relative to the first rigid object occurring between the first and second acquisition times;
provide a relative motion vector field defining the estimated relative motion of the second rigid object relative to the first rigid object based on the first registration and the second registration;
generate corrected 2D X-Ray projection data using the relative motion vector field to correct for the relative motion of the second rigid object relative to the first rigid object during acquisition of the input projection image sequence; and
generate motion-compensated 3D reconstruction data of the input projection image sequence based on the corrected 2D X-Ray projection data.

* * * * *